(12) United States Patent
Franz et al.

(10) Patent No.: US 9,175,016 B2
(45) Date of Patent: Nov. 3, 2015

(54) PROCHELATORS USEFUL FOR INHIBITING METAL-ASSOCIATED TOXICITY

(71) Applicant: Duke University, Durham, NC (US)

(72) Inventors: Katherine J. Franz, Durham, NC (US); Marina G. D. Leed, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/168,528

(22) Filed: Jan. 30, 2014

(65) Prior Publication Data
US 2014/0148414 A1    May 29, 2014

Related U.S. Application Data

(62) Division of application No. 13/386,441, filed as application No. PCT/US2010/042898 on Jul. 22, 2010, now Pat. No. 8,680,077.

(60) Provisional application No. 61/228,175, filed on Jul. 24, 2009.

(51) Int. Cl.
*A01N 55/08*   (2006.01)
*A61K 31/69*   (2006.01)
*C07F 5/02*    (2006.01)
*C07F 5/04*    (2006.01)

(52) U.S. Cl.
CPC .............. *C07F 5/027* (2013.01); *C07F 5/025* (2013.01); *C07F 5/04* (2013.01)

(58) Field of Classification Search
CPC ............ C07F 5/025; C07F 5/027; C07F 5/04
USPC ............... 514/13, 64; 546/13; 544/69, 229
See application file for complete search history.

(56) References Cited

U.S. PATENT DOCUMENTS

| 8,236,783 B2 | 8/2012 | Franz et al. | |
| 8,680,077 B2 * | 3/2014 | Franz et al. | 514/64 |
| 2006/0089380 A1 | 4/2006 | Barnham et al. | |
| 2009/0253161 A1 | 10/2009 | Franz et al. | |
| 2010/0004204 A1 | 1/2010 | Franz et al. | |
| 2011/0184333 A1 | 7/2011 | Franz et al. | |

OTHER PUBLICATIONS

Waggoner DJ et al. The role of copper in neurodegenerative disease. Neurobiology of Disease. 1999; 6: 221-230.
Horning MS et al. Endogenous mechanisms of neuroprotection: role of zinc, copper, and carnosine. Brain Research. 2000; 852: 56-61.
Mercer JFB. The molecular basis of copper-transport diseases. Trends in Molecular Medicine. Feb. 2001; 7(2): 64-69.
Opazo C et al. Metalloenzyme-like activity of Alzheimer's disease beta-amyloid. The Journal of Biological Chemistry. Oct. 25, 2002; 277(43): 40302-40308.
Yang W et al. Boronic acid compounds as potential pharmaceutical agents. Medicinal Research Reviews. 2003; 23(3): 346-368.
Charkoudian LK et al. A pro-chelator triggered by hydrogen peroxide inhibits iron-promoted hydroxyl radical formation. Journal of American Chemical Society. 2006; 128(38): 12424-1245.
Gaggelli E et al. Copper homeostasis and neurodegenerative disorders (Alzheimer's, prion, and Parkinson's diseases and amyotrophic lateral sclerosis). Chemical Reviews. 2006; 106(6): 1995-2044.
Charkoudian LK et al. Modifications of boronic ester pro-chelators triggered by hydrogen peroxide tune reactivity to inhibit metal-promoted oxidative stress. Dalton Transactions. 2007; 5031-5042.
Madsen E and Gitlin JD. Copper and iron disorders of the brain. The Annual Review of Neuroscience. 2007; 30: 317-337.
International Search Report and Written Opinion, PCT/US2010/042898, mailed Sep. 7, 2010.
Dickens MG and Franz KJ. A prochelator activated by hydrogen peroxide prevents metal-induced amyloid β aggregation. ChemBioChem. Jan. 4, 2010; 11(1): 59-62.
Charkoudian LK et al. Modifications of boronic ester pro-chelatores triggered by hydrogen peroxide tune reactivity to inhibit metal-promoted oxidative stress. Dalton Transactions. Nov. 21, 2007; 43: 5031-5042.

* cited by examiner

*Primary Examiner* — My-Chau T Tran
(74) *Attorney, Agent, or Firm* — Myers Bigel Sibley & Sajovec, P.A.

(57) ABSTRACT

Prochelator compounds of Formula I or Formula II:

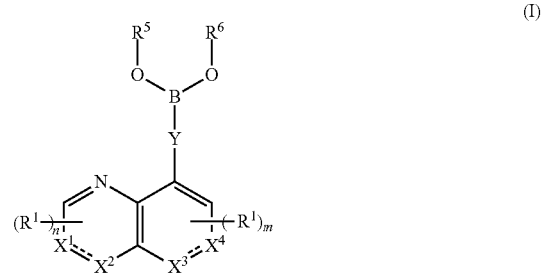

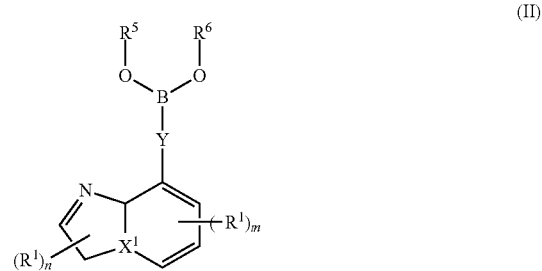

are described, along with methods of using the same and pharmaceutical formulations or compositions containing the same.

12 Claims, 5 Drawing Sheets

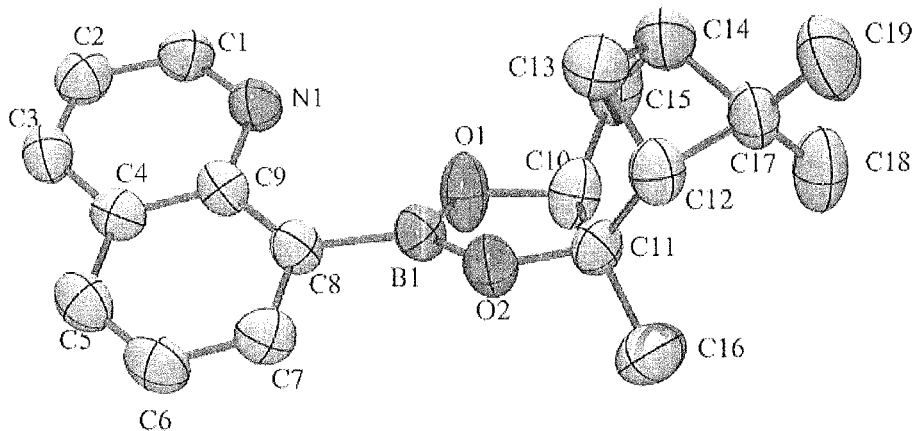
Figure 1. X-ray crystal structure of QBP.
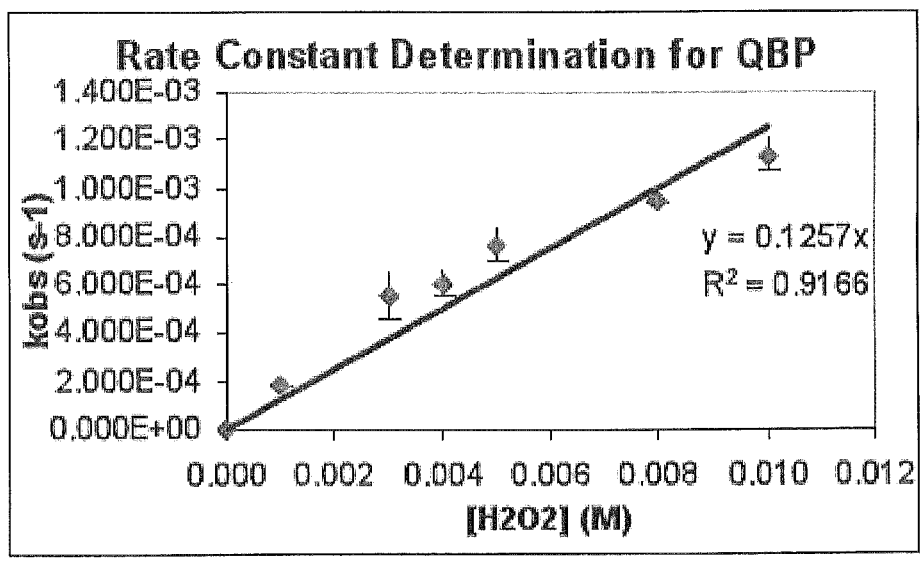
Figure 3. Plot of $k_{obs}$ at varying concentrations of $H_2O_2$ to obtain the rate constant $k$ for the conversion of QBP to HQ

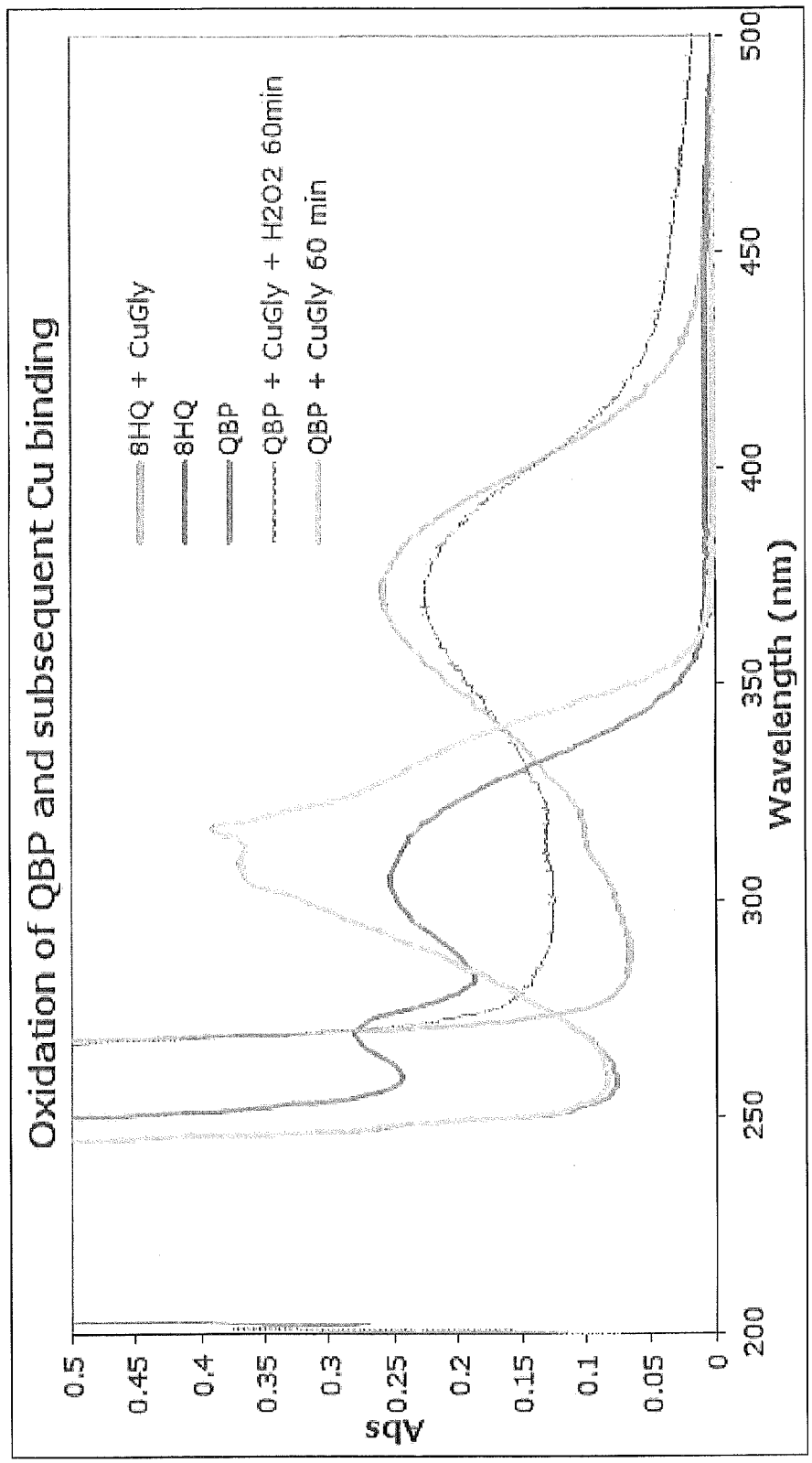
Figure 2. Oxidation and $Cu^{2+}$ binding by QBP.

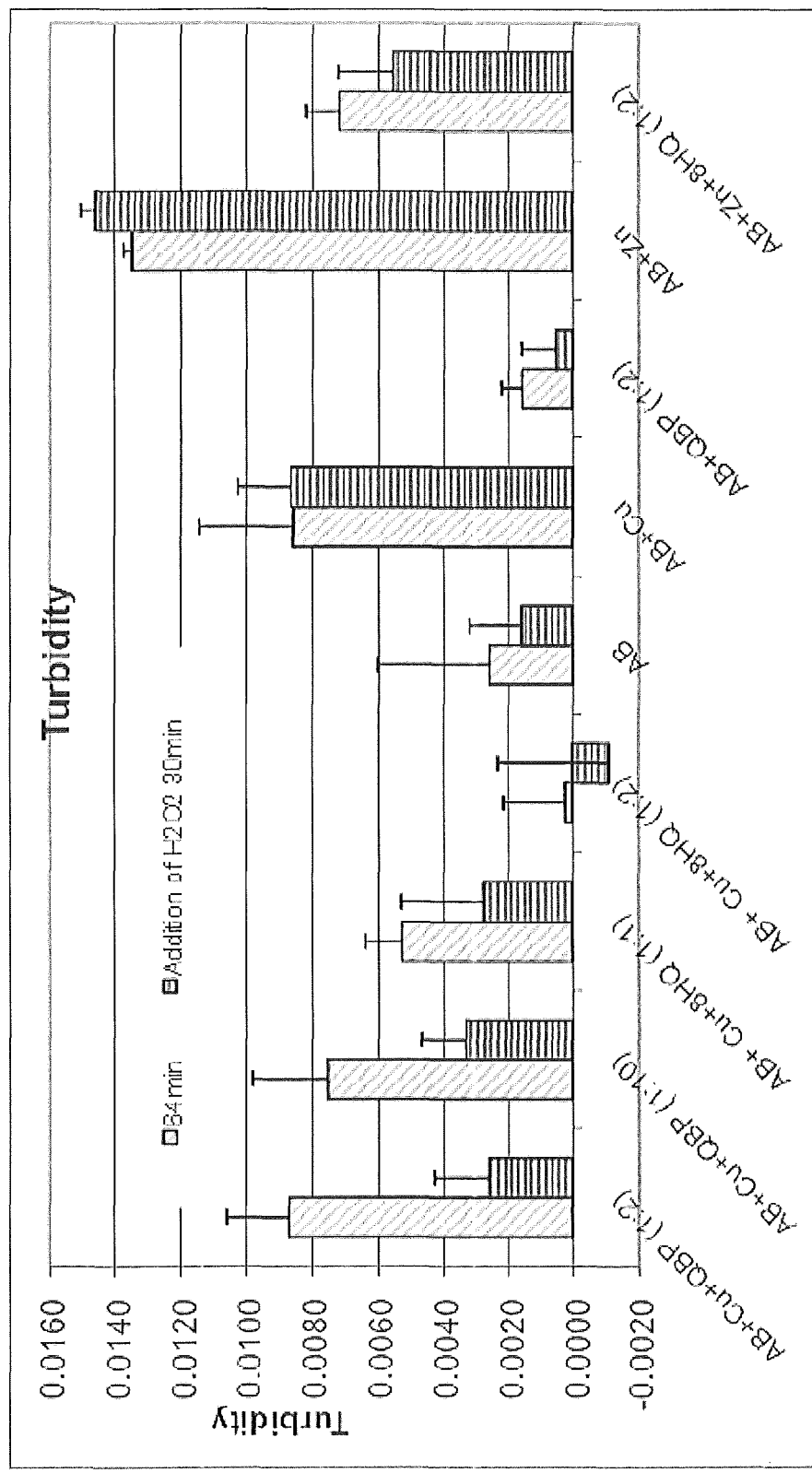
Figure 4. Turbidity assay between the sample and its matched control that does not contain Aβ.

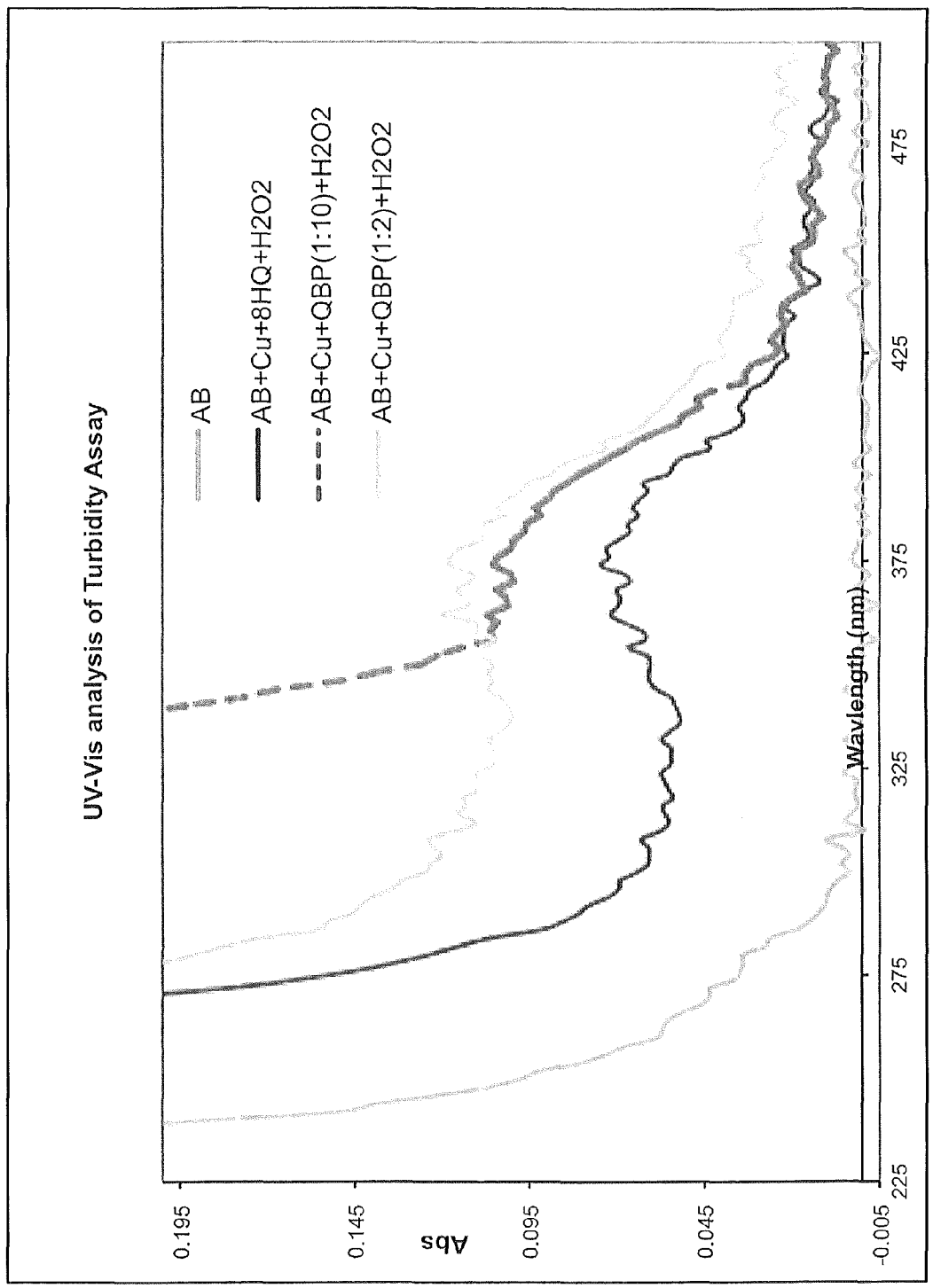
Figure 5. UV-vis analysis of H$_2$O$_2$-treated A$\beta$ samples.

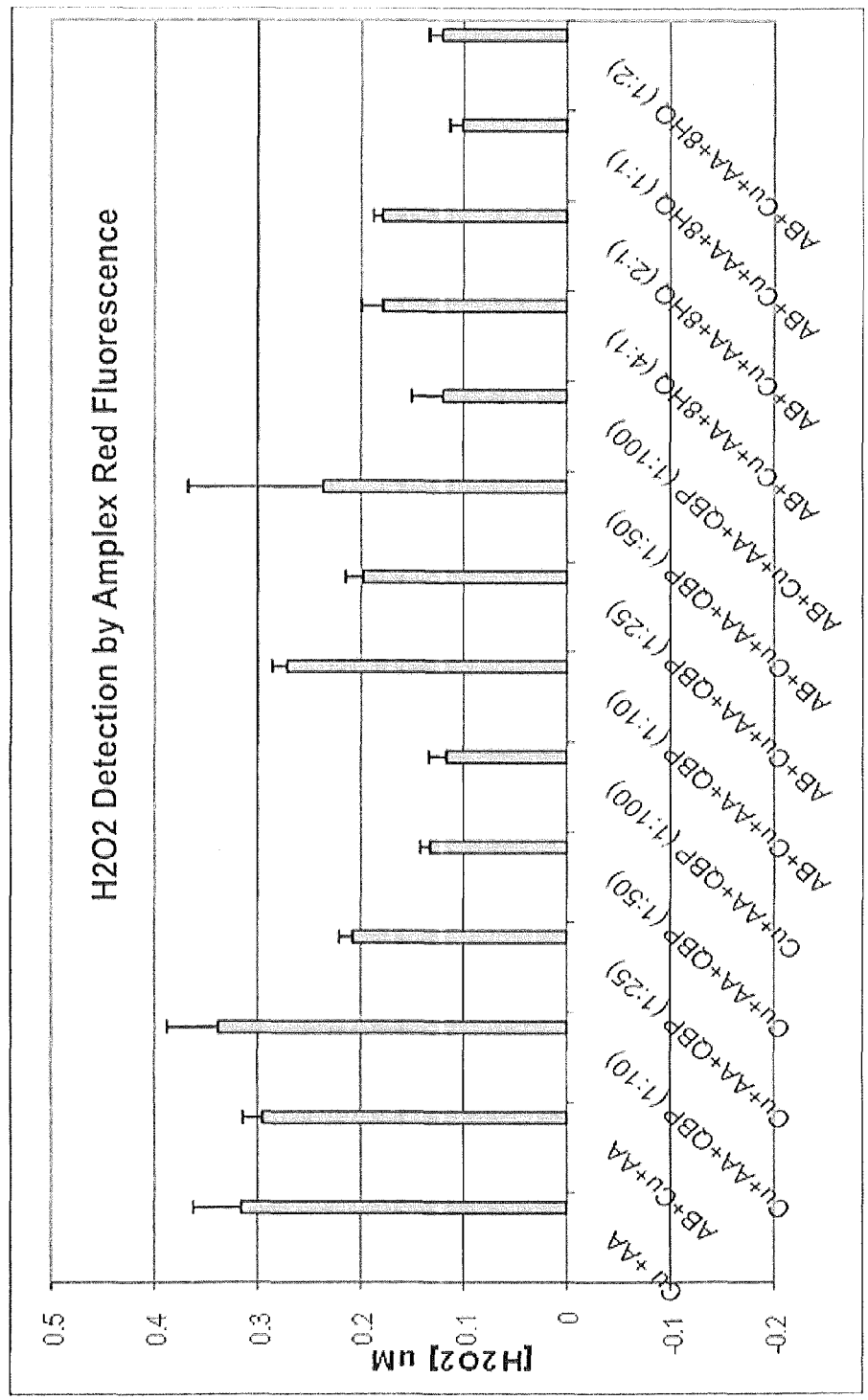
Figure 6. Hydrogen peroxide detection for samples containing various combinations of Aβ, Cu(Gly)₂, ascorbic acid QBP, and 8HQ.

PROCHELATORS USEFUL FOR INHIBITING METAL-ASSOCIATED TOXICITY

RELATED APPLICATIONS

This application is divisional of and claims priority to U.S. patent application Ser. No. 13/386,441, filed Feb. 24, 2012, now allowed, which is a 35 U.S.C. §371 national phase entry of PCT Application PCT/US2010/042898, filed Jul. 22, 2010, and published in English on Jan. 27, 2011, as International Publication No. WO 2011/011597 A1, and which claims the benefit under 35 U.S.C. §119(e) of U.S. Provisional Patent Application Ser. No. 61/228,175, filed Jul. 24, 2009, the disclosure of each of which is incorporated herein by reference in its entirety.

STATEMENT OF GOVERNMENT SUPPORT

This invention was made with Government support under NIH grant number 1RO1-GM084176-01. The Government has certain rights to this invention.

FIELD OF THE INVENTION

The present invention concerns transition metal binding agents, compositions containing and methods of using the same.

BACKGROUND OF THE INVENTION

Alzheimer's disease (AD) is a progressive and fatal brain disease that is the most common form of dementia. Its characteristic pathology includes extracellular amyloid plaques that form as a result of abnormal clearance and/or increased production of amyloid-β peptides (Aβ) that are released from the amyloid precursor protein (APP).[1,2] It is likely that the toxic forms of Aβ are not the intact plaques but rather soluble oligomers and prefibrillar assemblies that lead to oxidative stress and neuronal destruction.[3] Metal ions, particularly $Cu^{1+/2+}$ and $Zn^{2+}$ but also $Fe^{2+/3+}$, have been implicated in both processes related to Aβ pathology: peptide aggregation and formation of reactive oxygen species (ROS) that lead to oxidative stress.[4] Exactly how metals mediate these processes is not fully appreciated, and questions remain about the protective versus harmful roles that individual metals play under different conditions and at different stages of disease progression.

It is speculated that both APP and Aβ may have normal roles in copper homeostasis.[5,6] It has also been shown in vitro that Aβ can act as an antioxidant by quenching free radicals and by chelating Cu in a manner that minimizes its reactivity for catalyzing OH. from $H_2O_2$ via the Fenton reaction (Eq. 1).[7,8]

$Cu^+ + H_2O_2 \rightarrow Cu^{2+} + OH.$  Eq. 1

Other evidence, however, suggests that Aβ-Cu complexes are pro-oxidant and directly culpable of neurotoxicity. In vitro, Aβ in the presence of Cu or Fe and reducing agents like ascorbate produces $H_2O_2$, which can subsequently react with the reduced metal to produce hydroxyl radicals via the Fenton reaction.[9-11] Metal-mediated $H_2O_2$ generation appears at an early stage during in vitro Aβ aggregation,[11] which supports the notion that soluble Aβ-Cu species are responsible for the oxidative damage that is one of the earliest pathological events in AD.[12] Furthermore, copper has been shown to intensify Aβ toxicity in primary cortical neurons.[9,10,13] Like $Cu^{2+}$, $Zn^{2+}$ also promotes Aβ aggregation in vitro, but the Zn-induced aggregates appear to be neuroprotective, perhaps by displacing $Cu^{2+}$ and thereby suppressing $H_2O_2$ generation.[14-16]

An emerging hypothesis to reconcile the seemingly contradictory evidence related to metals, Aβ, and oxidative stress is that metal binding and Aβ aggregation may represent an initial, protective response to dampen ROS production. Excessive $H_2O_2$ production and an overburden of Cu could eventually push the system into a vicious cycle that switches Aβ-Cu activity from antioxidant to pro-oxidant.[17] During this stage, metal exchange with $Zn^{2+}$ could promote further Aβ aggregation as a defense against Cu-induced damage. While strong chelating agents are known to reverse metal-induced aggregates, this model suggests that disaggregating plaques alone could have the unintended consequence of exacerbating oxidative damage.[17]

Metal chelating agents have appeared as a compelling strategy for Alzheimer's disease therapies.[18] In particular, 8-hydroxyquinoline (8HQ) derivatives clioquinol and PBT2 have shown promising results in mouse models and in phase IIa clinical trials of Alzheimer's patients.[19,20] These compounds inhibit metal-induced Aβ aggregation and ROS generation.[21] It is thought that their primary mechanism of action is to redistribute extracellular metal ions to intracellular stores where they are required for biochemical function.[19]

While these reports are encouraging for the further development of metal-targeted compounds for neurodegenerative disease, concerns remain for the unintended consequences of manipulating metal distribution in the brain. New reagents are needed that can function as metal-binding agents that mitigate the damaging effects of metals while preserving their beneficial effects.

SUMMARY OF THE INVENTION

Herein, we disclose prochelators that are designed to bind metals only under conditions of oxidative stress. Given that elevated production of $H_2O_2$ by deviant Cu-Aβ interactions may be the trigger point for neurodegeneration, prochelators that are activated by $H_2O_2$ may be beneficial for managing a transition metal burden at locations of disease progression without stimulating widespread metal redistribution.

Provided herein are prochelator compounds of Formula I or Formula II:

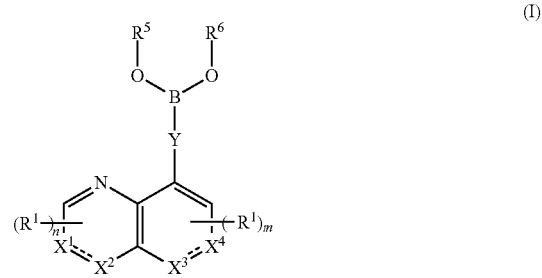

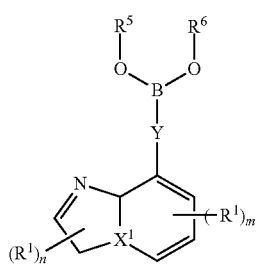

wherein:

Y is a covalent bond or —O—R$^7$—R$^8$—, where R$^7$ is —CH$_2$— or —CO$_2$CH$_2$— and R$^8$ is phenylene, which phenylene is unsubstituted or substituted 1, 2, 3 or 4 times with independently selected halo or alkyl;

n and m are each an integer from 1 to 3 (or in the case of Formula II n is an integer of from 1 to 2);

each R$^1$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

R$^5$ and R$^6$ are independently selected H, alkyl, or haloalkyl, or together form an alkylene bridge (e.g., a C2-C4 alkylene bridge, optionally containing a fused ring such as a cycloalkyl or aryl ring), which alkylene bridge may be unsubstituted or substituted from 1 to 4 times with alkyl, halo, a fused cycloalkyl and/or aryl ring;

each X$^1$ through X$^4$ in Formula I is independently selected from the group consisting of N, O, and CH; and X$^1$ in Formula II is N or CH;

dashed lines represent optional double bonds;

or a pharmaceutically acceptable salt or prodrug thereof.

Also provided are prochelator compounds selected from the group consisting of:

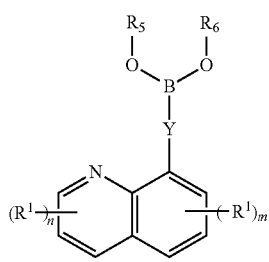

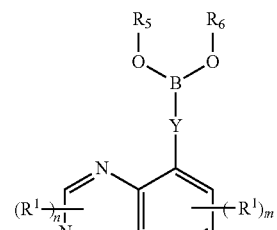

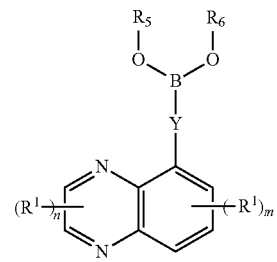

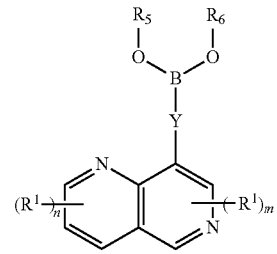

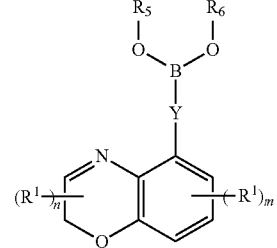

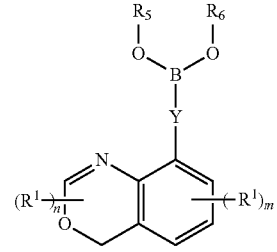

wherein:

Y is a covalent bond or —O—R$^7$—R$^8$—, where R$^7$ is —CH$_2$— or —CO$_2$CH$_2$— and R$^8$ is phenylene, which phenylene is unsubstituted or substituted 1, 2, 3 or 4 times with independently selected halo or alkyl.

n and m are each an integer from 1 to 3;

each R$^1$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy; and $R^5$ and $R^6$ are independently selected H, alkyl, or haloalkyl, or together form an alkylene bridge, which alkylene bridge may be unsubstituted or substituted from 1 to 4 times with alkyl, halo, a cycloalkyl or a fused aryl ring;

or a pharmaceutically acceptable salt or prodrug thereof.

In some embodiments of the above-mentioned formulas, $R^5$ and $R^6$ are independently selected H, alkyl, or haloalkyl.

In some embodiments, $R^5$ and $R^6$ together form an alkylene bridge, which alkylene bridge may be unsubstituted or substituted from 1 to 4 times with alkyl, halo, a fused cycloalkyl or a fused aryl ring.

In some embodiments of Formula I and Formula II, $R^5$ and $R^6$ together form a C2 alkylene bridge having a bicyclic cycloalkyl substituted thereon, which alkylene bridge and/or bicyclic cycloalkyl may be unsubstituted or substituted from 1 to 4 times with alkyl or halo.

In some embodiments, $R^5$ and $R^6$ together form a group:

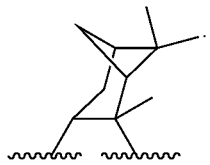 [SMILES: *C1CC2CC(C1(*)C)C2(C)C]

For example, provided is a compound:

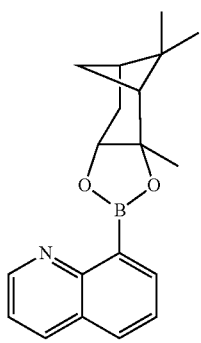 [SMILES: CC1(C)C2CC3OB(c4cccc5cccnc45)OC3(C)C1C2]

or a pharmaceutically acceptable salt or prodrug thereof.

Also provided are compositions comprising a compound given above and a pharmaceutically acceptable carrier.

Further provided are methods of making a boronic ester-masked 8-hydroxyquinoline comprising reacting a quinoline 8-boronic acid with a diol to form said boronic ester-masked 8-hydroxyquinoline. In some embodiments, the diol is a pinanediol.

Methods of binding copper in the presence of hydrogen peroxide are provided for a subject in need thereof, comprising administering to said subject a compounds given above in an amount effective to bind copper in the presence of hydrogen peroxide.

Methods of treating a neurodegenerative disease in a subject in need thereof are provided, comprising administering said subject a compound given above in a treatment effective amount. In some embodiments, the neurodegenerative disease is Alzheimer's disease.

Also provided is the use of a prochelator compound as described herein for the treatment of a neurodegenerative disease or a disease, disorder or trauma involving copper homeostasis.

Further provided is the use of a prochelator compound as described herein in the preparation of a medicament for carrying out a method of treatment as described herein.

The foregoing and other objects and aspects of the present invention are explained in greater detail in the drawings herein and the specification set forth below.

BRIEF DESCRIPTION OF THE DRAWINGS

FIG. 1. X-ray crystal structure of QBP.

FIG. 2. Oxidation and $Cu^{2+}$ binding by QBP. 100 μM QBP and 50 μM $Cu(Gly)_2$ were incubated in PBS buffer pH 7.4. After one hour, 4 mM $H_2O_2$ was added. After 60 min, oxidation and Cu binding were complete. Resulting spectrum is nearly identical to 8HQ-Cu spectra.

FIG. 3. Plot of $k_{obs}$ at varying concentrations of $H_2O_2$ to obtain the rate constant k for the conversion of QBP to HQ. QBP was initially dissolved in a minimal amount of methanol and then diluted into PBS buffer, pH 7.4, to a final concentration of 100 μM. Spectra were taken immediately after addition of 1-10 mM $H_2O_2$; at least 40 spectra were collected before 50% conversion of prochelator to chelator. The change in absorbance at 273 nm was used to follow the reaction. The negative slope of the linear fit of $\ln(1-(A-A_o/A_o))$ vs time gives the observed rate constant $k_{obs}$. The slope of the line through data $k_{obs}$ vs $[H_2O_2]$ provides k ($M^{-1} s^{-1}$).

FIG. 4. Turbidity assay, as monitored by the difference in absorbance at 405 nm between the sample and its matched control that does not contain Aβ. Samples, which contain various combinations of 10 μM Aβ, 10 μM $Cu(Gly)_2$, 10 μM $ZnCl_2$, 10 or 20 μM 8HQ, 20 or 100 μM QBA, 20 or 100 μM QBP, as indicated on the graph, were incubated in a 96 well plate at 37° C. Total volume per well was made up to 200 μL with Hepes buffer. Abs readings were taken 64 min after mixing (diagonal hashed bars). After one hour incubation, 1 mM $H_2O_2$ was added to each well and Abs readings were taken after 30 min (horizontal striped bars). Error bars represent the variability of triplicate measurements.

FIG. 5. UV-vis analysis of $H_2O_2$-treated Aβ samples. The samples are the same ones as in FIG. 4.

FIG. 6. Hydrogen peroxide detection by the Amplex Red/HRP assay for samples containing various combinations of 200 nm Aβ, 200 nm $Cu(Gly)_2$, 10 μM ascorbic acid, 2-200 μM QBP, 50-400 nm 8HQ, in a total volume of 50 μL buffer (50 mM hepes, 150 mM NaCl). Samples were incubated at 37° C. for approximately 1 h before 50 μL of Amplex Red/HRP reagent was added. Fluorescence readings were taken with $\lambda_{ex}$=485 and $\lambda_{em}$=590 nm.

DETAILED DESCRIPTION OF THE INVENTION

Herein are described prochelators that are designed to bind metals only under conditions of oxidative stress.[24-26] Given that elevated production of $H_2O_2$ by deviant Cu-Aβ interactions may be the trigger point for neurodegeneration, prochelators that are activated by $H_2O_2$ may be beneficial for managing a transition metal burden at locations of disease progression without stimulating widespread metal redistribution.

"Prochelators" as used herein are chelator compounds that are designed to bind one or more transition metals only under certain conditions, e.g., conditions of oxidative stress.

"Transition metal" as used herein refers to one of the 38 elements in groups 3 through 12 of the periodic table. In certain embodiments, the transition metals of this invention include, but are not limited to: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, etc.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, acylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene bridge" as used herein refers to a straight or branched chain hydrocarbon bridging species containing from 1 to 10 carbon atoms. Representative examples include, but are not limited to, C1-C5 bridges such as —(CH$_2$)$_n$— where n is 1 or 2 to 3, 4 or 5. The term "alkylene bridge" is intended to include both substituted and unsubstituted unless otherwise indicated and may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. Bicyclic and tricyclic ring systems are also included. These rings may be optionally substituted with additional substituents as described herein such as halo or loweralkyl. The term "cycloalkyl" is generic and intended to include heterocyclic groups as discussed below unless specified otherwise.

"Heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. In some embodiments aryl contains a "hetero" atom and is also a "heterocyclo" group as described above. The term "aryl" is intended to include both substituted and unsubstituted aryl unless otherwise indicated and these groups may be substituted with the same groups as set forth in connection with alkyl and loweralkyl above. More specifically, "aryl" groups as used herein may be substituted 1, 2, 3, or 4 or more times with independently selected halo (e.g., haloaryl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, acyloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Diol" as used herein refers to a chemical compound containing two hydroxyl groups.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Neurodegenerative disease" is a disease in which cells of the brain and/or spinal cord are lost. Known neurodegenerative diseases in which copper metabolism has been implicated include Alzheimer's disease, amyotrophic lateral sclerosis (ALS), Parkinson's disease, and human prion disease such as Creutzfeldt-Jakob disease. See, e.g., Gaggelli et al., Chemistry Reviews 106:1995-2044 (2006); Waggoner et al., Neurobiology of Disease 6:221-230 (1999); Mercer, Trends in Molecular Medicine, 7(2):64-69 (2001).

Other diseases, conditions or traumas known to involve copper include Wilson disease, Menkes disease, Pick's disease, and aceruloplasminemia. In addition, toxicity associated with copper and hydrogen peroxide include ischemic insults such as stroke, and seizures. See, e.g., Horning et al., Brain Research 852:56-61 (2000); Madsen et al. Annu. Rev. Neurosci. 30:317-337 (2007).

"Treat" as used herein refers to any type of treatment that imparts a benefit to a patient afflicted with a disease or disorder, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

"Cells" as used herein with respect to in vitro cultures or compositions include plant, animal, and microbial cells, such as mammalian, avian, reptile, protozoal, fungal, yeast, gram negative bacterial, gram positive bacterial, monocot, and dicot cells, etc.

The disclosures of all United States patent references cited herein are to be incorporated by reference herein in their entirety.

1. Active Compounds.

Provided herein are prochelators that are designed to bind metals preferentially under conditions of oxidative stress. In some embodiments, the prochelators are boronic ester-masked, which masks are removed under oxidative stress (e.g., in the presence of $H_2O_2$).

Active compounds include compounds of Formula I and Formula II:

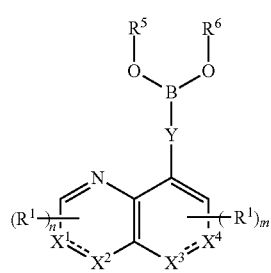

(I)

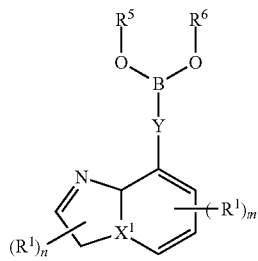

(II)

wherein:

Y is a covalent bond or —O—$R^7$—$R^8$—, where $R^7$ is —$CH_2$— or —$CO_2CH_2$— and $R^8$ is phenylene, which phenylene is unsubstituted or substituted 1, 2, 3 or 4 times with independently selected halo or alkyl;

n and m are each an integer from 1 to 3;

each $R^1$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

$R^5$ and $R^6$ are independently selected H, alkyl, or haloalkyl, or together form an alkylene bridge, which alkylene bridge may be unsubstituted or substituted from 1 to 4 times with alkyl, halo, a fused cycloalkyl or a fused aryl ring;

each X is independently selected from the group consisting of N, O, and CH; and dashed lines represent optional double bonds;

or a pharmaceutically acceptable salt or prodrug thereof.

In some embodiments of Formula I and Formula II, $R^5$ and $R^6$ are independently selected H, alkyl, or haloalkyl.

In some embodiments of Formula I and Formula II, $R^5$ and $R^6$ together form an alkylene bridge, which alkylene bridge may be unsubstituted or substituted from 1 to 4 times with alkyl, halo, a fused cycloalkyl or a fused aryl ring.

In some embodiments of Formula I and Formula II, $R^5$ and $R^6$ together form a C2 alkylene bridge having a bicyclic cycloalkyl substituted thereon, which bicyclic cycloalkyl may be unsubstituted or substituted from 1 to 4 times with alkyl or halo.

In some embodiments of Formula I and Formula II, $R^5$ and $R^6$ together form a group:

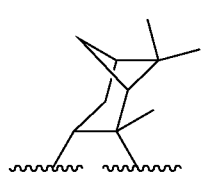 [SMILES: *C1CC2CC(C1(*)C)C2(C)C]

In some embodiments, the compound of Formula I is compound of Formula Ia, Formula Ib, Formula Ic, Formula Id, Formula Ie, or Formula If:

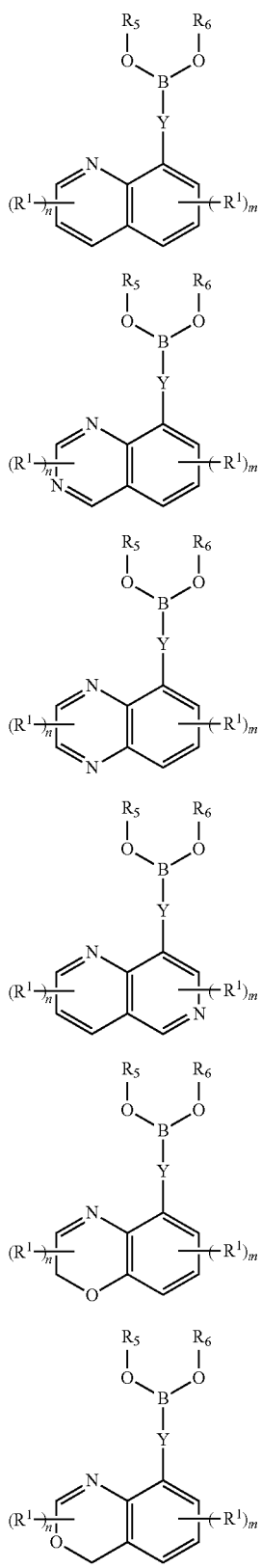

wherein:

Y is a covalent bond or —O—R[7]—R[8]—, where R[7] is —CH$_2$— or —CO$_2$CH$_2$— and R[8] is phenylene, which phenylene is unsubstituted or substituted 1, 2, 3 or 4 times with independently selected halo or alkyl;

n and m are each an integer from 1 to 3;

each R[1] is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, acyloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxyacylamino, and aminoacyloxy; and R[5] and R[6] are independently selected H, alkyl, or haloalkyl, or together form an alkylene bridge, which alkylene bridge may be unsubstituted or substituted from 1 to 4 times with alkyl, halo, a fused cycloalkyl or a fused aryl ring;

or a pharmaceutically acceptable salt or prodrug thereof.

In some embodiments of Formula Ia, Formula Ib, Formula Ic, Formula Id, Formula Ie, or Formula If, R[5] and R[6] are independently selected H, alkyl, or haloalkyl.

In some embodiments of Formula Ia, Formula Ib, Formula Ic, Formula Id, Formula Ie, or Formula If, R[5] and R[6] together form an alkylene bridge, which alkylene bridge may be unsubstituted or substituted from 1 to 4 times with alkyl, halo, cycloalkyl (e.g., a bicyclic cycloalkyl), or a fused aryl ring.

In some embodiments of Formula I, R[5] and R[6] together form a C2 alkylene bridge having a bicyclic cycloalkyl substituted thereon, which alkylene bridge and/or bicyclic cycloalkyl may be unsubstituted or substituted from 1 to 4 times with alkyl or halo.

In some embodiments of Formula Ia, Formula Ib, Formula Ic, Formula Id, Formula Ie, or Formula If, R[5] and R[6] together form a group:

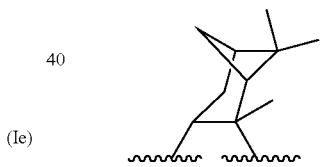

In some embodiments of Formula Ia, the active compound is a compound:

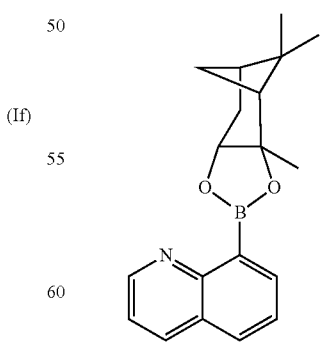

or a pharmaceutically acceptable salt or prodrug thereof.

The active compounds disclosed herein can, as noted above, be prepared in the form of their salts, including for some purposes pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Pharmaceutically acceptable prodrugs as used herein refers to those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. As a general proposition, a dosage from about 0.1 or 1.0 to about 250 or 500 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 200 mg/kg may be employed for oral administration. Typically, a dosage from about 1 mg/kg to 100 mg/kg may be employed for intramuscular injection. The duration of the treatment is usually once per day for a period of two to three weeks or until the condition is essentially controlled. Lower doses given less frequently can be used prophylactically to prevent or reduce the incidence of recurrence of the disease.

The present invention is explained in greater detail in the following non-limiting Examples.

EXAMPLES

We herein demonstrate that a boronic ester-masked 8-hydroxyquinoline derivative that we have termed QBP converts to 8HQ in the presence of $H_2O_2$. Once converted to 8HQ, it is available for coordinating metal ions, as shown in Scheme 1 for Cu2+.

Scheme 1. Oxidation of QBP and $H_2O_2$ and subsequent binding of copper by 8-hydroxyquinoline (8HQ).

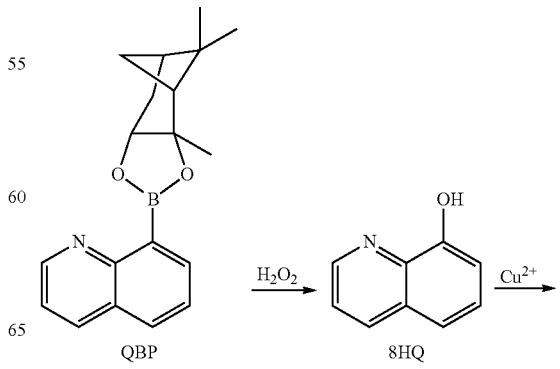

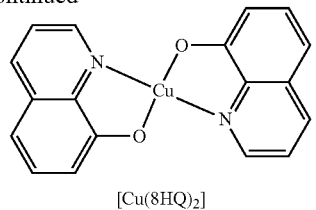

[Cu(8HQ)₂]

Quinoline boronic acid (QBA) is commercially available. Preliminary investigations of using it as a prochelator revealed that it interacts directly with metal ions. In order to prevent premature metal binding, it was therefore necessary to form a boronic ester. Initial attempts to cap QBA with pinacol were unsuccessful and resulted in isolation of an insoluble, dehydrated dimer of QBA. Reaction of QBA with pinanediol in a Dean Stark apparatus, however, was successful and gave a good yield of the desired boronic ester, QBP. The X-ray crystal structure is shown in FIG. 1.

Once isolated, QBP is stable in aqueous solution between pH 5-8 with no signs of hydrolysis to QBA over the course of 10 h, as monitored by UV-Vis and mass spectrometry. At low and high pH values outside of this window, some hydrolysis to QBA was detected by mass spectrometry.

With the phenol of 8HQ masked by the pinanediol boronic ester, the QBP prochelator should have little to no affinity for metal ions. A comparison of the UV-vis spectra in FIG. 2 of QBP alone or in the presence of $Cu^{2+}$ for an hour reveals no change in spectral features and validates the assumption that QBP does not interact with $Cu^{2+}$ in its prochelator form. Addition of $H_2O_2$, however, causes a new spectrum to appear that matches that of $[Cu(8HQ)_2]$, consistent with Scheme 1 given above.

In order to determine the rate of conversion of QBP to 8HQ by $H_2O_2$ (Eq. 2), reactions were monitored spectrophotometrically under pseudo first-order conditions of excess $H_2O_2$. The observed rate constants ($k_{obs}$) were plotted against peroxide concentration (FIG. 3) to give a rate constant k of 0.13 $M^{-1} s^{-1}$.

$$\text{rate}=k[QBP][H_2O_2] \qquad \text{Eq. 2}$$

To demonstrate further that the prochelator QBP does not interact with metal ions, we monitored the metal-induced aggregation of Aβ☐ by a light scattering assay. The results in FIG. 4 show that, as previously observed by others, both $Cu^{2+}$ and $Zn^{2+}$ induce aggregation of Aβ, with $Zn^{2+}$ causing a more profound effect.

The presence of 2 equiv of 8HQ completely inhibits the copper-induced aggregation and significantly reduces zinc-induced aggregation. QBP, on the other hand, does not interfere with metal-induced Aβ☐ aggregation. Because $Zn^{2+}$ may provide a protective effect, it may not be desirable to prevent Zn-promoted Aβ☐ aggregation, per se.

In order to show that 8HQ that is generated in situ from QPB and $H_2O_2$ is capable of reversing Aβ☐ aggregation, 1 mM $H_2O_2$ was added to each of the sample wells in FIG. 4 that had already incubated for an hour and contained metal-aggregated Aβ. The horizontal striped bars in FIG. 4 show that $H_2O_2$, alone, does not reduce the turbidity of samples containing Aβ☐ and $Cu^{2+}$, nor does it increase the turbidity of samples containing Aβ ☐alone or Aβ/$Cu^{2+}$/8HQ. These results show that $H_2O_2$, itself, does not influence the aggregation state of Aβ. In contrast, samples that contain Aβ/$Cu^{2+}$/QBP show a significant decrease in turbidity 30 min following $H_2O_2$ addition. This result is consistent with conversion of QBP to 8HQ, which can subsequently bind $Cu^{2+}$ and reverse Aβ ☐aggregation.

Given the concentrations of QBP and $H_2O_2$ present in the samples and the rate constant for prochelator-to-chelator conversion, this reaction is predicted to generate 5 to 20 μM 8HQ, depending on the initial QBP concentration. The highest concentration is certainly sufficient for complete binding of $Cu^{2+}$ in a 1:2 chelated complex, although as shown in the Figure, even the lower concentration is effective.

Further confirmation that $Cu(8HQ)_2$ is, indeed, generated in the reaction of Aβ/Cu/QBP/$H_2O_2$ described in FIG. 4 comes from the UV-vis spectrum of the reaction mixture, shown in FIG. 5.

The complex $[Cu(8HQ)_2]$ has a characteristic absorbance band at 375 nm, which is clearly visible in samples that contain Aβ, $Cu^{2+}$ and 8HQ. The samples that contain Aβ/Cu/QBP/$H_2O_2$ also show this characteristic peak, verifying that $[Cu(8HQ)_2]$ has, indeed, been generated during the course of the incubation. Mass spectral analysis of the sample gives m/z of 352, further confirming formation of $[Cu(8HQ)_2]$ in these complex mixtures. The previous experiment contained a relatively high concentration (1 mM) of $H_2O_2$ that was added in a single bolus. Several groups have shown that combinations of Aβ, Cu and reductants produce significant amounts of $H_2O_2$ from $O_2$. Therefore, to investigate whether these conditions of more biologically relevant $H_2O_2$ production are sufficient for activating QPB, samples of Aβ, $Cu^{2+}$ (provided as Cu(Gly)$_2$), ascorbic acid, and either 8HQ or QBP were monitored for $H_2O_2$ production with the Amplex Red assay. FIG. 6 shows the concentration of $H_2O_2$ detected by Amplex Red after a 1-h incubation of 200 nM Cu(Gly)$_2$, 200 nM Aβ, 10 μM ascorbic acid and either 8HQ or QBP over a range of concentrations in Hepes buffer at pH 7.4. Samples that contain Cu and ascorbate (with or without Aβ) provide just over 300 nM detectable $H_2O_2$. This result shows that Aβ☐neither prevents nor promotes $H_2O_2$ production by Cu under these conditions when compared to Cu in the presence of glycine as a carrier ligand. In contrast, 8HQ inhibits $H_2O_2$ production, even when present at only a quarter of an equiv of Cu. When 8HQ is present at a 2:1 ratio to Cu, the amount of detectable $H_2O_2$ diminishes to one third that detected in the presence of Aβ. This result confirms that 8HQ coordinates Cu in a manner that diminishes its ability to catalyze $H_2O_2$ from $O_2$ in the presence of reductant. When QBP is added to the reaction mixture in place of 8HQ, a similar result is obtained. As shown in FIG. 6, samples that contain 100 μM QBP along with Cu, ascorbate, and Aβ☐ result in detection of about 100 nM $H_2O_2$, which is a third of the concentration obtained in the absence of chelator and similar to that obtained in the presence of 200-400 nM 8HQ.

A current hypothesis about Alzheimer's disease is that oxidative stress is an early event in disease progression and that copper may be a culprit in promoting further oxidative damage. The results presented here indicate that prochelator QBP can be activated under conditions that mimic early Alzheimer's pathology where copper, Aβ, and biological reductants exacerbate ROS formation. Importantly, the prochelator, itself does not prevent or disaggregate metal-promoted Aβ☐ aggregates if they are not accompanied by elevated $H_2O_2$. This feature may be beneficial because Aβ aggregation, itself, may play a protective role, and it may not be desirable to disaggregate plaques that are already formed. Once activated to its unmasked form, however, the released 8HQ diminishes copper's ROS-forming reactivity and inhibits further Aβ☐ aggregation.

Example 2

Preparation of B-DIP Prochelator

Materials and Instrumentation

All chemicals and solvents were obtained from Sigma-Aldrich and used as received unless otherwise noted. The 2-bromo-1-[4-(dimethylamino)]phenyl-ethanone was obtained from Combi-Blocks Inc. (San Diego, Calif.) and 2-amino-3-boronic acid (pinacol ester)pyridine was obtained from Boron Molecular (Research Triangle, N.C.). NMR data were collected on a Varian Inova 400 MHz (1H) with chemical shifts reported in ppm and J values in Hz. High-resolution, fast-atom, bombardment (HR-FABMS) mass spectra were recorded on a JOEL JMS-SX-102 instrument.

Scheme 1. Structures of BP-DIP, B-DIP, and O-DIP and their reaction product, Chelator 1, upon exposure to hydrogen peroxide. The synthesis of BP-DIP and B-DIP are described below.

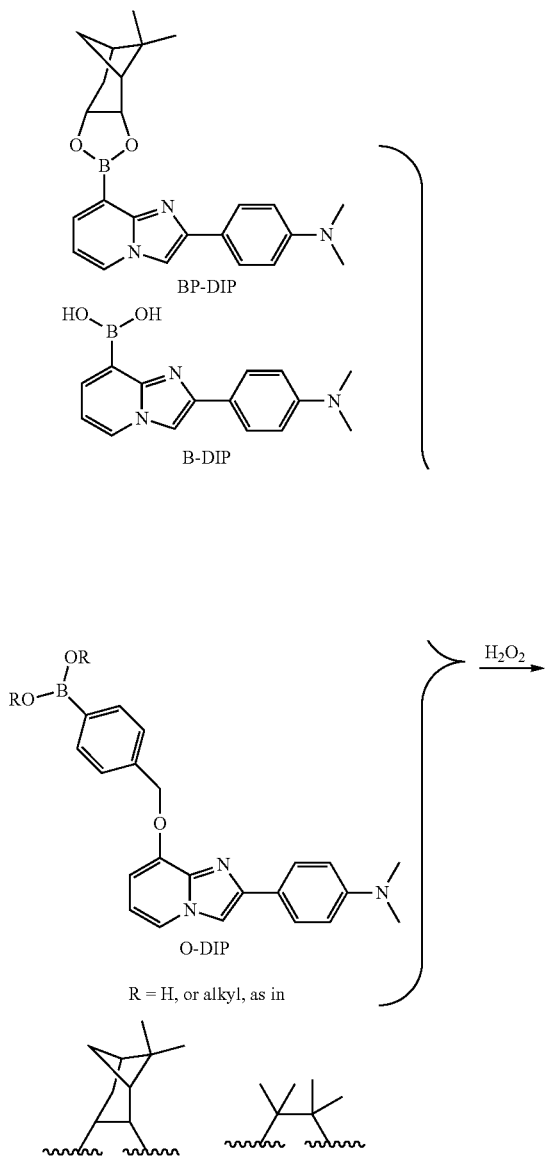

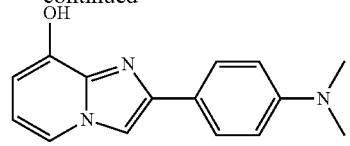

Chelator-1
(see: S. S. Hindo, A. M. Mancino, J. J. Braymer, Y. Liu, S. Vivekanadan, A. Ramamoorthy and M. H. Lim, *J. Am. Chem. Soc.*, 2009, 131, 16663-16665

Synthesis: 2-[4-(dimethylamino)phenyl]imidazo[1,2,a]pyridine-8-boronic acid, (B-DIP)

2-amino-3-boronic acid (pinacol ester)pyridine (1 mmol, 220 mg) was combined with acetonitrile (4 mL) in a round bottom flask and slowly heated with stirring to 75° C. under reflux. Once the solution mixture reached 75° C., a 0.5-mL aliquot of 2-bromo-1-[4-(dimethylamino)]phenyl-ethanone (0.9 mmol, 216 mg dissolved in 2 mL of acetonitrile) was added to the mixture and the clear orange solution was refluxed for 30 minutes. The reaction mixture was monitored by silica thin layer chromatography plates and after the disappearance of 2-bromo-1-[4-(dimethylamino)]phenyl-ethanone another aliquot (0.5 mL) of 2-bromo-1-[4-(dimethylamino)]phenyl-ethanone was added. As the reaction mixture refluxes a bright yellow precipitate forms. This process of slow addition of 2-bromo-1-[4-(dimethylamino)]phenyl-ethanone was continued until all of the 2-bromo-1-[4-(dimethylamino)]phenyl-ethanone had been added to the reaction mixture and completely reacted. After the mixture was cooled on an ice bath for 30 minutes, the precipitate was collected by filtration, washed with ether, and dried under vacuum to obtain a bright yellow powder. The crude product was purified by affinity chromatography on N,N, diethanolaminomethyl polystyrene (DEAM-PS). Following the specific package instructions of loading ratio of product to solid support, a 100 mg portion of crude B-DIP dissolved in 40 mL of anhydrous tetrahydrofuran was added to the solid support resin loaded into a 50-mL, oven-dried reaction vessel having a medium porosity fritted glass bottom. The vessel was agitated on an orbital shaker for 2 hours, after which the vessel was drained to collect a clear orange solution. The resin was washed eight times with anhydrous tetrahydrofuran (20 mL) until the filtrate was clear and colorless; the whole time keeping the solution under minimum exposure to the atmosphere. The product was eluted from the solid-support by addition of tetrahydrofuran/2% $H_2O$ (40 mL) and stirring the mixture for an hour on the orbital shaker. Following filtration, the solvent was removed by evaporation to yield a light brown product. $^1$H NMR (400 MHz, d6-DMSO)/δ (ppm): 9.11 (s, 1H), 8.57 (d, J=6.57 Hz, 1H), 8.22 (s, 1H), 7.77 (d, J=8.71 Hz, 2H), 7.65 (d, J=6.43 Hz, 1H), 6.95 (t, J=6.68, 6.68 Hz, 1H), 6.81 (d, J=8.76 Hz, 2H), 2.95 (s, 6H) Calcd for [M+H]$^+$, 282.13. Found, 282.1.

Synthesis: 2-[4-(dimethylamino)phenyl]imidazo[1,2,a]pyridine-8-boronic acid, pinanediol (BP-DIP)

A 1 mmol portion of B-DIP was combined with 1 mmol (1R,2R,3S,5R)-(−)-pinanediol in 2.4 mL of DMSO and 18 mL of toluene. The clear yellow-orange liquid was refluxed in a Dean-Stark apparatus for 14 hours leading to a dark brown solution. Solvent was removed by evaporation. Calcd for [M+H]$^+$, 416.3. Found 416.3.

Scheme 2. Synthesis of B-DIP
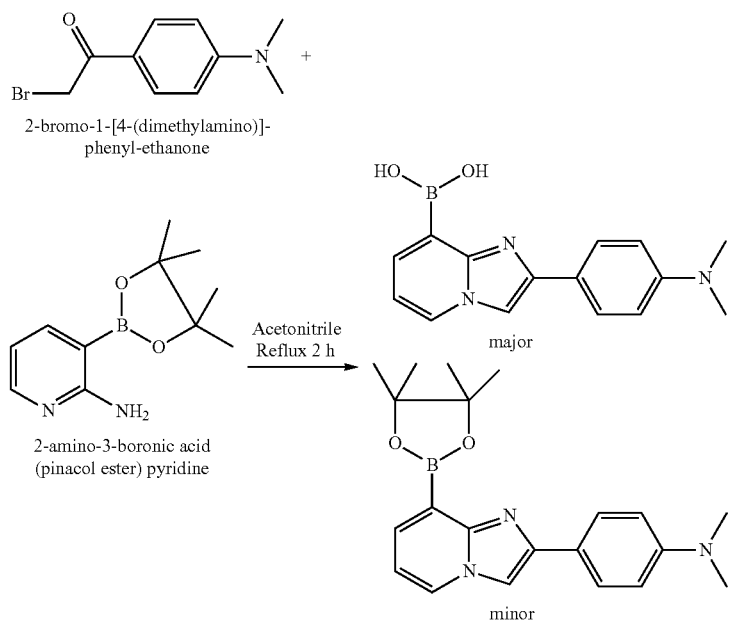
Scheme 3. Purification of boronic acid derivatives by affinity chromatography on solid support N, N, Diethanolaminomethyl polystyrene (DEAM-PS).
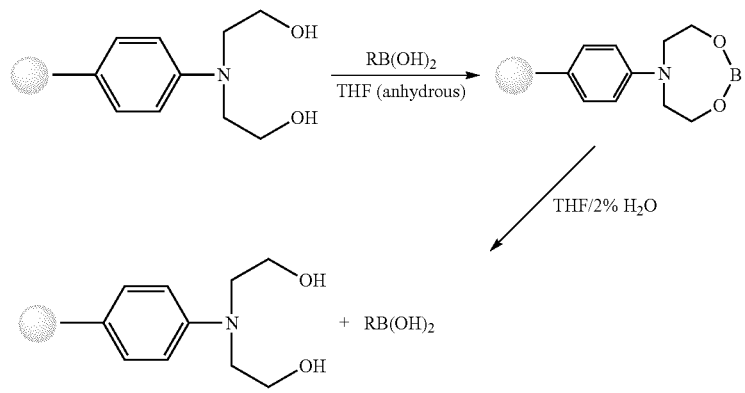
Scheme 4. Synthesis of DPP Prochelator, Boronic ester, Pinanediol (BP-DIP).
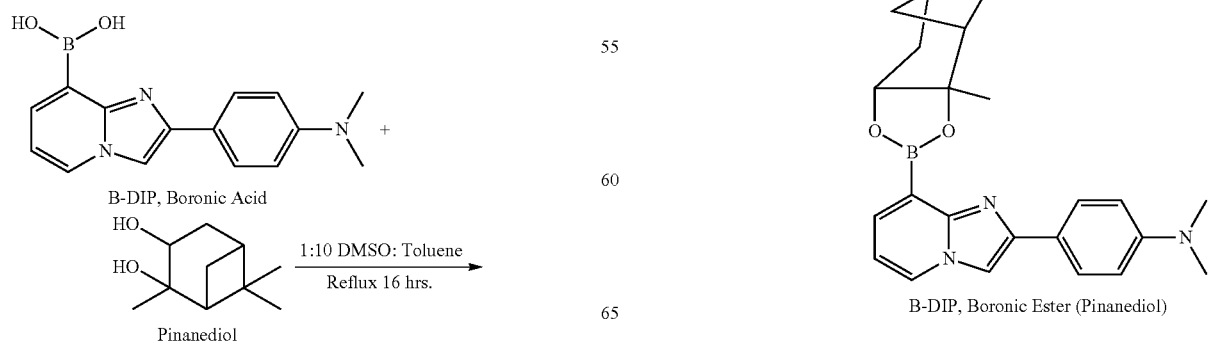

REFERENCES

1. Hardy, J.; Selkoe, D. J., The Amyloid Hypothesis of Alzheimer's Disease: Progress and Problems on the Road to Therapeutics. *Science* 2002, 297, (5580), 353-356.
2. Roychaudhuri, R.; Yang, M.; Hoshi, M. M.; Teplow, D. B., Amyloid {beta}-Protein Assembly and Alzheimer Disease. *J. Biol. Chem.* 2009, 284, (8), 4749-4753.
3. Rauk, A., Why is the amyloid beta peptide of Alzheimer's disease neurotoxic? *Dalton Transactions* 2008, (10), 1273-1282.
4. Bush, A. I., The metallobiology of Alzheimer's disease. *Trends in Neurosciences* 2003, 26, (4), 207-214.
5. Gaggelli, E.; Kozlowski, H.; Valensin, D.; Valensin, G., Copper Homeostasis and Neurodegenerative Disorders (Alzheimer's, Prion, and Parkinson's Diseases and Amyotrophic Lateral Sclerosis). *Chem. Rev.* 2006, 106, (6), 1995-2044.
6. Treiber, C.; Simons, A.; Strauss, M.; Hafner, M.; Cappai, R.; Bayer, T. A.; Multhaup, G., Clioquinol mediates copper uptake and counteracts copper efflux activities of the amyloid precursor protein of Alzheimer's disease. *J. Biol. Chem.* 2004, 279, (50), 51958-51964.
7. Baruch-Suchodolsky, R.; Fischer, B., Aβ40, either Soluble or Aggregated, Is a Remarkably Potent Antioxidant in Cell-Free Oxidative Systems. *Biochemistry* 0, (0).
8. Zou, K.; Gong, J.-S.; Yanagisawa, K.; Michikawa, M., A Novel Function of Monomeric Amyloid beta-Protein Serving as an Antioxidant Molecule against Metal-Induced Oxidative Damage. *J. Neurosci.* 2002, 22, (12), 4833-4841.
9. Huang, X.; Cuajungco, M. P.; Atwood, C. S.; Hartshorn, M. A.; Tyndall, J. D. A.; Hanson, G. R.; Stokes, K. C.; Leopold, M.; Multhaup, G.; Goldstein, L. E.; Scarpa, R. C.; Saunders, A. J.; Lim, J.; Moir, R. D.; Glabe, C.; Bowden, E. F.; Masters, C. L.; Fairlie, D. P.; Tanzi, R. E.; Bush, A. I., Cu(II) Potentiation of Alzheimer Abeta Neurotoxicity. CORRELATION WITH CELL-FREE HYDROGEN PEROXIDE PRODUCTION AND METAL REDUCTION. *J. Biol. Chem.* 1999, 274, (52), 37111-37116.
10. Opazo, C.; Huang, X.; Cherny, R. A.; Moir, R. D.; Roher, A. E.; White, A. R.; Cappai, R.; Masters, C. L.; Tanzi, R. E.; Inestrosa, N. C.; Bush, A. I., Metalloenzyme-like Activity of Alzheimer's Disease beta-Amyloid. Cu-DEPENDENT CATALYTIC CONVERSION OF DOPAMINE, CHOLESTEROL, AND BIOLOGICAL REDUCING AGENTS TO NEUROTOXIC H2O2. *J. Biol. Chem.* 2002, 277, (43), 40302-40308.
11. Tabner, B. J.; El-Agnaf, O. M. A.; Turnbull, S.; German, M. J.; Paleologou, K. E.; Hayashi, Y.; Cooper, L. J.; Fullwood, N. J.; Allsop, D., Hydrogen Peroxide Is Generated during the Very Early Stages of Aggregation of the Amyloid Peptides Implicated in Alzheimer Disease and Familial British Dementia. *J. Biol. Chem.* 2005, 280, (43), 35789-35792.
12. Castellani, R. J.; Honda, K.; Zhu, X. W.; Cash, A. D.; Nunomura, A.; Perry, G.; Smith, M. A., Contribution of redox-active iron and copper to oxidative damage in Alzheimer disease. *Ageing Research Reviews* 2004, 3, (3), 319-326.
13. Smith, D. P.; Smith, D. G.; Curtain, C. C.; Boas, J. F.; Pilbrow, J. R.; Ciccotosto, G. D.; Lau, T.-L.; Tew, D. J.; Perez, K.; Wade, J. D.; Bush, A. I.; Drew, S. C.; Separovic, F.; Masters, C. L.; Cappai, R.; Barnham, K. J., Copper-mediated Amyloid-beta Toxicity Is Associated with an Intermolecular Histidine Bridge. *J. Biol. Chem.* 2006, 281, (22), 15145-15154.
14. Cuajungco, M. P.; Goldstein, L. E.; Nunomura, A.; Smith, M. A.; Lim, J. T.; Atwood, C. S.; Huang, X.; Farrag, Y. W.; Perry, G.; Bush, A. I., Evidence that the beta-Amyloid Plaques of Alzheimer's Disease Represent the Redox-silencing and Entombment of Abeta by Zinc. *J. Biol. Chem.* 2000, 275, (26), 19439-19442.
15. Cardoso, S. M.; Rego, A. C.; Pereira, C.; Oliveira, C. R., Protective effect of zinc on amyloid-beta 25-35 and 1-40 mediated toxicity. *Neurotox. Res.* 2005, 7, (4), 273-281.
16. Meloni, G.; Sonois, V.; Delaine, T.; Guilloreau, L.; Gillet, A.; Teissie, J.; Faller, P.; Vasak, M., Metal swap between Zn7-metallothionein-3 and amyloid-[beta]-Cu protects against amyloid-[beta] toxicity. *Nat Chem Biol* 2008, 4, (6), 366-372.
17. Atwood, C. S.; Obrenovich, M. E.; Liu, T.; Chan, H.; Perry, a; Smith, M. A.; Martins, R. N., Amyloid-[beta]: a chameleon walking in two worlds: a review of the trophic and toxic properties of amyloid-[beta]. *Brain Research Reviews* 2003, 43, (1), 1-16.
18. Bush, A. I., Drug Development Based on the Metals Hypothesis of Alzheimer's Disease. *J. Alzheimers Dis.* 2008, 15, (2), 223-240.
19. Adlard, P. A.; Cherny, R. A.; Finkelstein, D. I.; Gautier, E.; Robb, E.; Cortes, M.; Volitakis, I.; Liu, X.; Smith, J. P.; Perez, K.; Laughton, K.; Li, Q.-X.; Charman, S. A.; Nicolazzo, J. A.; Wilkins, S.; Deleva, K.; Lynch, T.; Kok, G.; Ritchie, C. W.; Tanzi, R. E.; Cappai, R.; Masters, C. L.; Barnham, K. J.; Bush, A. I., Rapid Restoration of Cognition in Alzheimer's Transgenic Mice with 8-Hydroxy Quinoline Analogs Is Associated with Decreased Interstitial A[beta]. *Neuron* 2008, 59, (1), 43-55.
20. Ritchie, C. W.; Bush, A. I.; Mackinnon, A.; Macfarlane, S.; Mastwyk, M.; MacGregor, L.; Kiers, L.; Cherny, R.; Li, Q.-X.; Tammer, A.; Carrington, D.; Mavros, C.; Volitakis, I.; Xilinas, M.; Ames, D.; Davis, S.; Beyreuther, K.; Tanzi, R. E.; Masters, C. L., Metal-Protein Attenuation With Iodochlorhydroxyquin (Clioquinol) Targeting A{beta} Amyloid Deposition and Toxicity in Alzheimer Disease: A Pilot Phase 2 Clinical Trial. *Arch Neurol* 2003, 60, (12), 1685-1691.
21. Cherny, R. A.; Atwood, C. S.; Xilinas, M. E.; Gray, D. N.; Jones, W. D.; McLean, C. A.; Barnham, K. J.; Volitakis, I.; Fraser, F. W.; Kim, Y.-S.; Huang, X.; Goldstein, L. E.; Moir, R. D.; Lim, J. T.; Beyreuther, K.; Zheng, H.; Tanzi, R. E.; Masters, C. L.; Bush, A. I., Treatment with a Copper-Zinc Chelator Markedly and Rapidly Inhibits [beta]-Amyloid Accumulation in Alzheimer's Disease Transgenic Mice. *Neuron* 2001, 30, (3), 665-676.
22. Madsen, E.; Gitlin, J. D., Copper and Iron Disorders of the Brain. *Annu. Rev. Neurosci.* 2007, 30, (1), 317-337.
23. Benvenisti-Zarom, L.; Chen, J.; Regan, R. F., The oxidative neurotoxicity of clioquinol. *Neuropharmacology* 2005, 49, (5), 687-694.
24. Charkoudian, L. K.; Dentchev, T.; Lukinova, N.; Wolkow, N.; Dunaief, J. L.; Franz, K. J., Iron Prochelator BSIH Protects Retinal Pigment Epithelial Cells against Cell Death Induced by Hydrogen Peroxide. *J. Inorg. Biochem.* 2008, 102, (12), 2130-2135.
25. Charkoudian, L. K.; Pham, D. M.; Franz, K. J., A prochelator triggered by hydrogen peroxide inhibits iron-promoted hydroxyl radical formation. *J. Am. Chem. Soc.* 2006, 128, (38), 12424-12425.
26. Charkoudian, L. K.; Pham, D. M.; Kwan, A.; Vangeloff, A.; Franz, K. J., Modifications of boronic ester pro-chelators triggered by hydrogen peroxide tune reactivity to inhibit metal-promoted oxidative stress. *Dalton Trans.* 2007, (43), 5031-5042.

That which is claimed is:

1. A compound of Formula II:

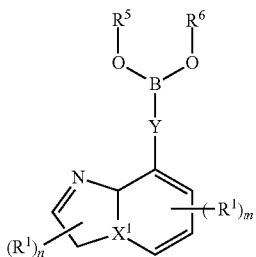

wherein:
- Y is a covalent bond or —O—$R^7$—$R^8$—, where $R^7$ is —$CH_2$— or —$CO_2CH_2$— and $R^8$ is phenylene, which phenylene is unsubstituted or substituted from 1 to 4 times with independently selected halo or alkyl;
- n and m are each an integer from 1 to 3;
- each $R^1$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;
- $R^5$ and $R^6$ are independently selected H, alkyl, or haloalkyl, or together form an alkylene bridge, which alkylene bridge may be unsubstituted or substituted from 1 to 4 times with alkyl, halo, cycloalkyl, aryl, a fused cycloalkyl or a fused aryl ring;
- $X^1$ is selected from the group consisting of N, O, and CH; and
- dashed lines represent optional double bonds;

or a pharmaceutically acceptable salt or prodrug thereof.

2. The compound of claim 1, wherein Y is a covalent bond.

3. The compound of claim 1, wherein Y is a covalent bond or —O—$R^7$—$R^8$—, where $R^7$ is —$CH_2$— or —$CO_2CH_2$— and $R^8$ is phenylene.

4. The compound of claim 1, wherein $R^5$ and $R^6$ are independently selected H, alkyl, or haloalkyl.

5. The compound of claim 1, wherein $R^5$ and $R^6$ together form an alkylene bridge, which alkylene bridge may be unsubstituted or substituted from 1 to 4 times with alkyl, halo, cycloalkyl, aryl, a fused cycloalkyl or a fused aryl ring.

6. The compound of claim 1, wherein $R^5$ and $R^6$ together form a C2 alkylene bridge having a bicyclic cycloalkyl substituted thereon, which C2 alkylene bridge and/or bicyclic cycloalkyl may be unsubstituted or substituted from 1 to 4 times with alkyl or halo.

7. The compound of claim 1, wherein $R^5$ and $R^6$ together form a group:

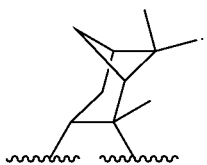 [SMILES: *C1CC2CC(C1(*)C)C2(C)C]

8. The compound of claim 1, wherein said compound has the formula:

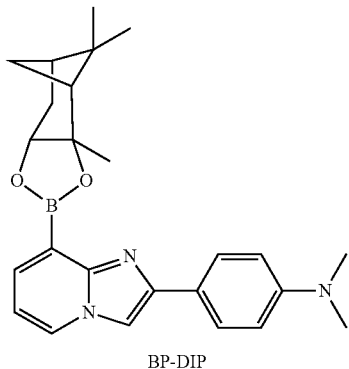

BP-DIP or a pharmaceutically acceptable salt or prodrug thereof.

9. A composition comprising a compound of claim 1 and a pharmaceutically acceptable carrier.

10. A method of binding copper in the presence of hydrogen peroxide in a subject in need thereof, comprising administering to said subject a compound of claim 1 in an amount effective to bind copper in the presence of hydrogen peroxide.

11. A method of treating a neurodegenerative disease in a subject in need thereof, comprising administering said subject a compound of claim 1 in a treatment effective amount.

12. The method of claim 11, wherein said neurodegenerative disease is Alzheimer's disease.

* * * * *